(12) United States Patent
Peszynski et al.

(10) Patent No.: US 7,529,393 B2
(45) Date of Patent: *May 5, 2009

(54) GUIDANCE OF INVASIVE MEDICAL DEVICES BY WIDE VIEW THREE DIMENSIONAL ULTRASONIC IMAGING

(75) Inventors: Michael Peszynski, Newburyport, MA (US); Ivan Salgo, Andover, MA (US); Bernard Savord, Andover, MA (US); Steven Scampini, Bedford, MA (US)

(73) Assignee: Koninklijke Philips Electronics, N.V. (NL)

( * ) Notice: Subject to any disclaimer, the term of this patent is extended or adjusted under 35 U.S.C. 154(b) by 644 days.

This patent is subject to a terminal disclaimer.

(21) Appl. No.: 10/550,210

(22) PCT Filed: Mar. 4, 2004

(86) PCT No.: PCT/IB2004/000708

§ 371 (c)(1),
(2), (4) Date: Sep. 21, 2005

(87) PCT Pub. No.: WO2004/086082

PCT Pub. Date: Oct. 7, 2004

(65) Prior Publication Data

US 2006/0182320 A1    Aug. 17, 2006

Related U.S. Application Data

(60) Provisional application No. 60/458,778, filed on Mar. 27, 2003.

(51) Int. Cl.
*G06K 9/00* (2006.01)

(52) U.S. Cl. ...................................... 382/128; 382/284

(58) Field of Classification Search .................. 382/128, 382/284; 600/443, 461
See application file for complete search history.

(56) References Cited

U.S. PATENT DOCUMENTS

| 5,817,022 | A | 10/1998 | Vesely |
| 5,873,830 | A | 2/1999 | Hossack et al. |
| 5,957,844 | A * | 9/1999 | Dekel et al. .................. 600/439 |
| 6,019,724 | A | 2/2000 | Gronningsaeter et al. |
| 6,221,016 | B1 * | 4/2001 | Hayakawa .................. 600/443 |
| 6,256,529 | B1 | 7/2001 | Holupka et al. |
| 6,375,617 | B1 | 4/2002 | Fraser |
| 6,398,736 | B1 | 6/2002 | Seward |
| 6,485,425 | B2 | 11/2002 | Seward et al. |
| 6,515,657 | B1 | 2/2003 | Zanelli |
| 6,544,187 | B2 | 4/2003 | Seward |

(Continued)

FOREIGN PATENT DOCUMENTS

EP    1 245 191    10/2002

*Primary Examiner*—John B Strege
(74) *Attorney, Agent, or Firm*—W. Brinton Yorks, Jr.

(57) ABSTRACT

A three dimensional ultrasonic diagnostic imaging system is operated to guide or observe the operation of an invasive medical device (30) in three dimensions. The invasive medical device (30) is shown in a detailed ultrasonic image and the balance of the volumetric region (120) in which the device is located is shown in a wide field of view. The detailed and wide fields of view may be displayed separately or overlapping in spatial alignment on an image display (18). The wide field of view may be shown in two or three dimensions. A quantified display may be shown together with the wide and detailed anatomical displays. The detailed view may also be shown in an enlarged or zoomed format.

19 Claims, 17 Drawing Sheets

U.S. PATENT DOCUMENTS

| | | |
|---|---|---|
| 6,556,695 B1 | 4/2003 | Packer et al. |
| 6,821,256 B2 | 11/2004 | Ackerman et al. |
| 2002/0049375 A1 * | 4/2002 | Strommer et al. ........... 600/407 |
| 2003/0028113 A1 | 2/2003 | Broadstone et al. |
| 2004/0097806 A1 | 5/2004 | Hunter et al. |

* cited by examiner

GUIDANCE OF INVASIVE MEDICAL DEVICES BY WIDE VIEW THREE DIMENSIONAL ULTRASONIC IMAGING

CROSS REFERENCE TO RELATED APPLICATION

This application claims the benefit of U.S. provisional application Ser. No. 60/458,778 filed Mar. 27, 2003, which is incorporated herein by reference.

This invention relates to ultrasonic diagnostic imaging and, more particularly, to the use of three dimensional ultrasonic diagnostic imaging to guide the placement and operation of invasive (interventional) medical devices in the body.

Ultrasonic imaging is commonly used to image the insertion, use or operation of medical devices and instruments within the body. One such common use of ultrasound imaging is in the conduct of a biopsy procedure. An ultrasound probe is used to image the pathology of interest for the procedure such as a suspected tumor or cyst. The probe is manipulated until the pathology is visible in the image plane. A biopsy needle attachment for the probe then guides the insertion of the biopsy needle within the image plane and toward the pathology. The clinician follows the travel of the needle in the ultrasound image, being careful to keep the probe stationary and the needle within the image plane until the needle tip reaches the pathology. A specimen is extracted through the needle and the needle is withdrawn from the body. Ultrasonic imaging is thus used to guide the travel of the needle into the body and to observe the conduct of the biopsy procedure.

Biopsy needles have been designed with their own ultrasonic transmitters or receivers which interact with the imaging probe. Such ultrasonically responsive needles allow the needle and the imaging probe to signal each other and enable the needle and its tip to be more clearly identified in the ultrasound image plane. Ultrasonically responsive biopsy needles are described in U.S. Pat. No. 5,158,088, for instance.

The planar imaging techniques are limited in that they provide a restricted, single image view of the internal site of the procedure. It would be desirable to provide a greater field of view of the site of the procedure to enable the clinician or surgeon to better guide and conduct the procedure. Improved imaging would assist biopsy procedures and also facilitate a wide range of invasive procedures such as the placement of stents and cannulae, the dilation or resection of vessels, treatments involving the heating or freezing of internal tissues, the placement of radioactive seeds or prosthetic devices such as valves and rings, the guidance of wires or catheters through vessels for the placement of devices such as pacemakers, implantable cardiovertors/defibrillators, electrodes, and guide wires, the placement of sutures, staples and chemical/gene sensing electrodes, the guidance or operation of robotic surgical devices, and the guidance of endoscopic or minimally invasive surgical procedures. Ultrasonic guidance would thus find expanded use in a broad range of invasive or interventional clinical applications including cardiac, pulmonary, central and peripheral nervous system procedures, gastrointestinal, musculoskeletal, gynecological, obstetrical, urological, ophthalmologic and otorhinolaryngologic procedures.

In accordance with the principles of the present invention, three dimensional ultrasonic imaging is used to guide or monitor the conduct of the placement and/or use of invasive (interventional) medical devices such as those enumerated above. In one embodiment the location of the interventional device or its activities are recorded in a three dimensional ultrasound image which consolidates information from both the three dimensional ultrasonic imaging system and the interventional system. The consolidated image may be viewed on the ultrasound system, on the interventional system, or on the display of a combined ultrasonic imaging and interventional device system. The interventional device is shown in a detailed ultrasonic image and the balance of the volumetric region in which the device is located is shown in a wide field of view. The detailed and wide fields of view may be displayed separately or overlapping in spatial alignment on an image display. The wide field of view may be shown in two or three dimensions. In accordance with a further aspect of the present invention the locus of the interventional device is ultrasonically scanned in greater detail than the surrounding volume for greater visual precision and higher frame rate of display of the guidance or use of the interventional device.

Figure 1:
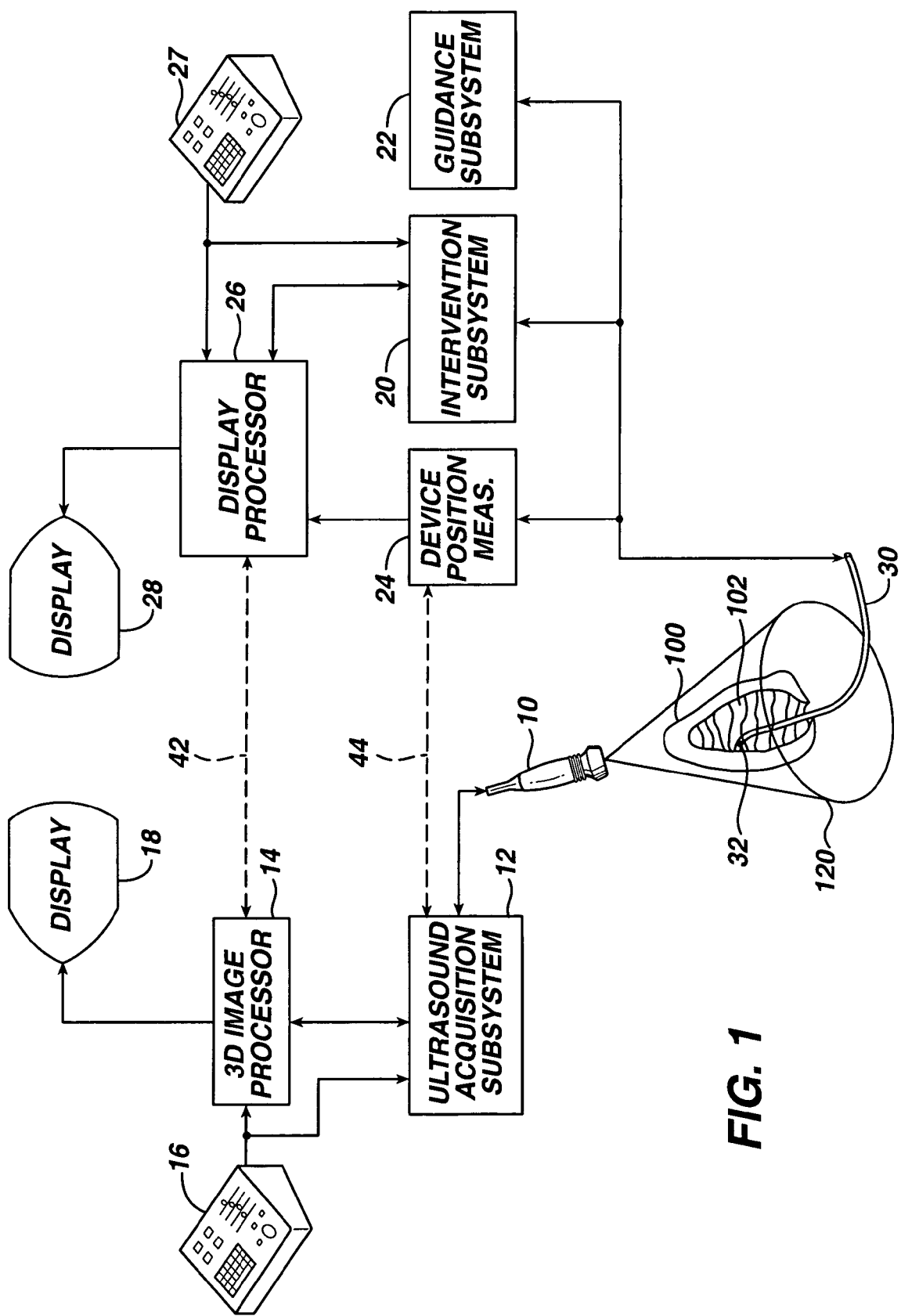
FIG. 1 illustrates in block diagram form the use of three dimensional ultrasonic imaging to guide or monitor an invasive instrument and procedure.

Referring first to FIG. 1, the use of three dimensional ultrasonic imaging to guide or monitor an invasive instrument and procedure is shown in partial block diagram form. On the left side of the drawing is a three dimensional (3D) ultrasonic imaging system including a probe 10 having a two dimensional array transducer. The transducer array transmits ultrasonic beams over a volumetric field of view 120 under control of an ultrasound acquisition subsystem 12 and receives echoes in response to the transmitted beams which are coupled to and processed by the acquisition subsystem. The echoes received by the elements of the transducer array are combined into coherent echo signals by the acquisition subsystem and the echo signals along with the coordinates from which they are received ($r,\theta,\phi$ for a radial transmission pattern) are coupled to a 3D image processor 14. The 3D image processor processes the echo signals into a three dimensional ultrasonic image which is displayed on a display 18. The ultrasound system is controlled by a control panel 16 by which the user defines the characteristics of the imaging to be performed.

Also shown in FIG. 1 is an interventional device system. The interventional device system includes an invasive (interventional) device 30 which performs a function within the body. In this drawing the interventional device is shown as a catheter, but it could also be some other tool or instrument such as a needle, a surgical tool such as a dissection instrument or stapler or a stent delivery, electrophysiology, or balloon catheter, a therapy device such as a high intensity ultrasound probe or a pacemaker or defibrillator lead, a diagnostic or measurement device such as an IVUS or optical catheter or sensor, or any other device which is manipulated and operates within the body. The interventional device 30 is manipulated by a guidance subsystem 22 which may mechanically assist the maneuvering and placement of the interventional device within the body. The interventional device 30 is operated to perform its desired function such as placing an item at a desired location, or measuring, illuminating, heating, freezing, or cutting tissue under the control of an interventional subsystem 20. The interventional subsystem 20 also received information from the interventional device on the procedure being performed, such as optical or acoustic image information, temperature, electrophysiologic, or other measured information, or information signaling the completion of an invasive operation. Information which is susceptible of processing for display is coupled to a display processor 26. The interventional device may also have an active position sensor 32 which is used to provide information as to the location of the working tip within the body. The active position sensor 32 may operate by transmitting or receiving signals in the acoustic, optical, radio frequency or electromagnetic spectrum and its output is coupled to a device position measurement subsystem 24. Alternately the sensor 32 may be a passive device such as a diffraction grating which is highly reflective of ultrasonic energy transmitted by the probe 10. Position information of the interventional device is coupled to the display processor 26 when appropriate for the processing or display of information concerning the position of the interventional within the body. Information pertinent to the functioning or operation of the interventional device is displayed on a display 28. The interventional device system is operated by a user through a control panel 27.

In the embodiment of FIG. 1 the invasive device 30 is shown as a catheter which is performing a function at the wall of the left ventricle 102 of the heart 100. The full extent of the endocardial wall of the left ventricle is visible by three dimensional ultrasonic imaging of the volumetric field of view 120 of the 3D ultrasonic imaging system. The working tip of the interventional device 30 may include an x-ray, r.f. or ultrasonic device for imaging or ranging the endocardium, or a physiologic or thermal sensor which conducts diagnostic measurements of the endocardium, or an ablation device which treats lesions on the endocardium, or a placement device for an electrode, for example. The tip of the interventional device is manipulated to a point on the heart wall where such a function is to be performed by operation of the guidance subsystem 22. The interventional device is then commanded to perform its intended procedure by the interventional subsystem 20, and the location at which the procedure is performed by the device position measurement subsystem 24 which receives or transmits a signal from the sensor 32 at the time of the procedure, for instance.

The invasive procedure may be assisted by monitoring the procedure simply by visualizing the site of the procedure, the wall of the left ventricle in the foregoing example, by use of the three dimensional ultrasound system. As the interventional device 30 is manipulated within the body the three dimensional environment in which the device is operated can be visualized in three dimensions, enabling the operator to anticipate turns and bends of orifices and vessels in the body and to precisely place the working tip of the interventional device at the desired site of the procedure. It is necessary to see a large field of view in order to provide gross navigation with enough detailed resolution to guide the intervention within the vicinity of the invasive device. The operator can maneuver and reposition the probe 10 to constantly keep the interventional device 30 within the probe's volumetric field of view. Since in the preferred embodiment the probe 10 has a two dimensional array which rapidly transmits and receives electronically steered beams, rather than a mechanically swept transducer, real time three dimensional ultrasonic imaging can be performed and the interventional device and its procedure observed continuously and precisely in three dimensions.

In accordance with a further aspect of this first embodiment of the present invention, a signal path 42 connects the ultrasound acquisition subsystem 12 of the ultrasound system and the device position measurement subsystem 24 of the interventional device system to allow synchronization of the imaging system and the interventional device. This synchronization allows image acquisition and interventional device operation to be done at different time interleaved intervals if the operation of one device would interfere with the other. For example, if the interventional device 30 is performing acoustic imaging of the heart or vessel wall, it is desirable for these acoustic intervals to occur when they will not be disrupted by acoustic transmissions from the 3D imaging probe 10. It may be desirable to suspend imaging when the interventional device is transmitting high energy signals for ablation or some other procedure that would interfere with the imaging signals from the probe 10. The synchronization also enables the ultrasound system to ask for and receive position information from the interventional device when the ultrasound system is producing a 3D ultrasound image with an enhanced representation of the position of the interventional device shown in the 3D ultrasound image. The ultrasound system may also ask for and receive position information from the interventional device when the ultrasound system is recording the location of a procedure performed by the interventional device for future reference, as will be discussed more fully below.

In accordance with a another aspect of this first embodiment of the present invention, image data may be exchanged over a signal path 44 between the 3D image processor 14 of the ultrasound system and the display processor 26 of the interventional device system for the formation of a 3D image containing information from both systems. This enables the display of an image of the interventional device 30, produced by the interventional device system, as part of a 3D ultrasound image produced by the ultrasound system. Such a fusion of the imaging capabilities of both systems better enables the physician to guide and utilize the interventional device, aided by the extensive three dimensional field of view afforded by the ultrasound system and the device image data produced by the interventional device system.

Figure 2:
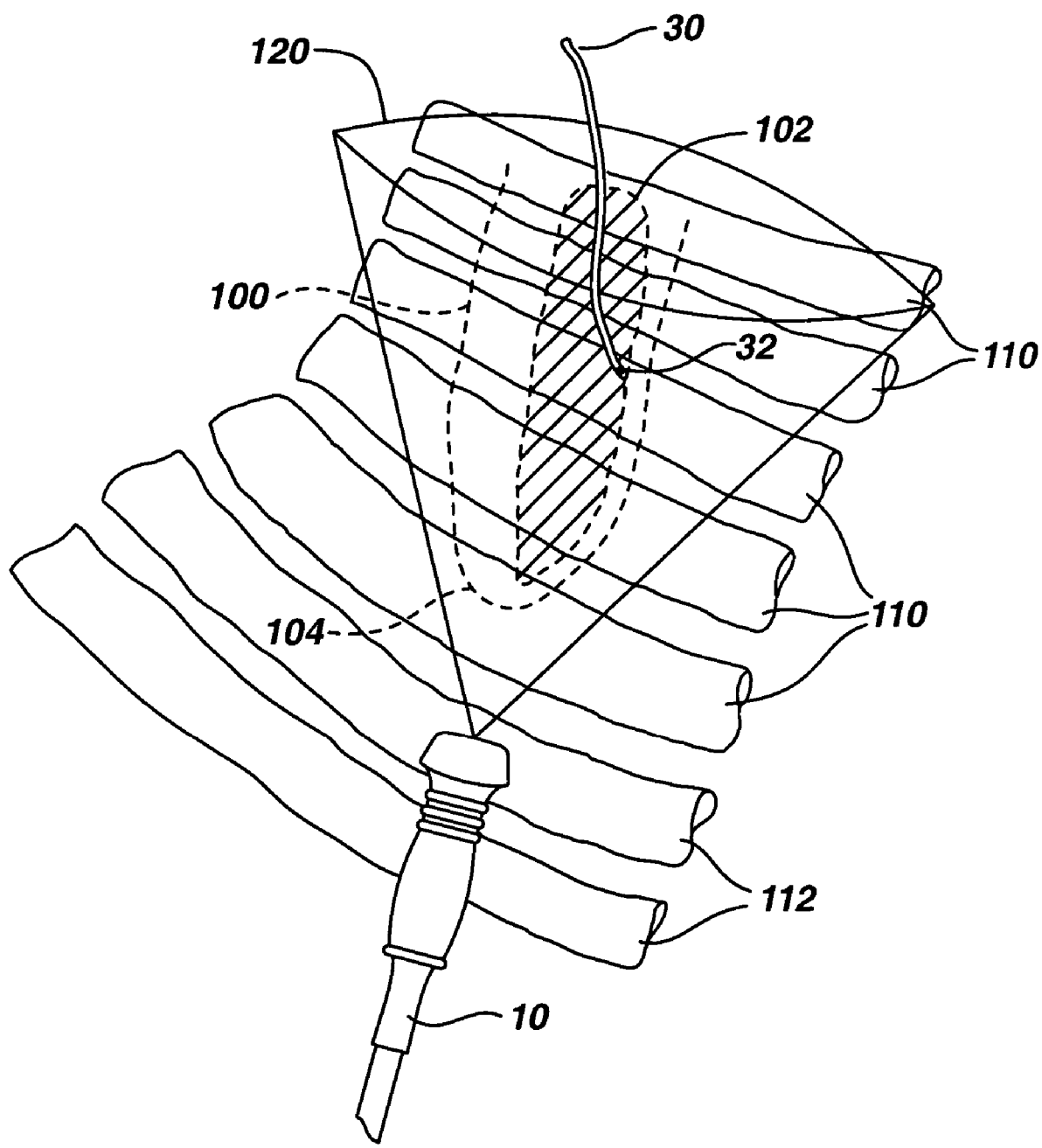
FIG. 2 illustrates the three dimensional ultrasonic imaging of a catheter in the heart by a transthoracic transducer probe.

FIG. 2 illustrates practice of the present invention when the three dimensional ultrasound probe used is a transthoracic probe 10. In this example the heart 100, shown in partial outline behind the rib cage 110,112, is located behind the left side of the rib cage. Outlined within the heart and crosshatched is the left ventricle 102 of the heart 100. The left ventricle can be accessed for ultrasonic imaging by scanning the heart from between the ribs 110,112 for adult patients and, for some pediatric patients, by scanning upward from below the lowest rib 112. The probe 10 scans the heart from the heart apex 104 as indicated by the outline 120 of the volumetric field of view scanned by the probe 10. As FIG. 2 illustrates, the left ventricle 102 can be fully encompasses and scanned by the volumetric field of view directed from between the rib cage 110,112. While this embodiment illustrates phased array scanning of the volumetric region 120 in a conical field of view, one skilled in the art will recognize that other scan formats may also be employed such as those which scan a rectangular or hexagonal pyramidal field of view. It will also be appreciated that probes other than transthoracic probes may be used for three dimensional scanning such as transesophageal probes, intracavity probes such as vaginal or rectal probes, and intervascular probes such as catheter-mounted transducer probes. While an electronically scanned two dimensional array transducer is preferred, mechanically scanned arrays may be preferred for some applications such as abdominal procedures.

Figure 3:
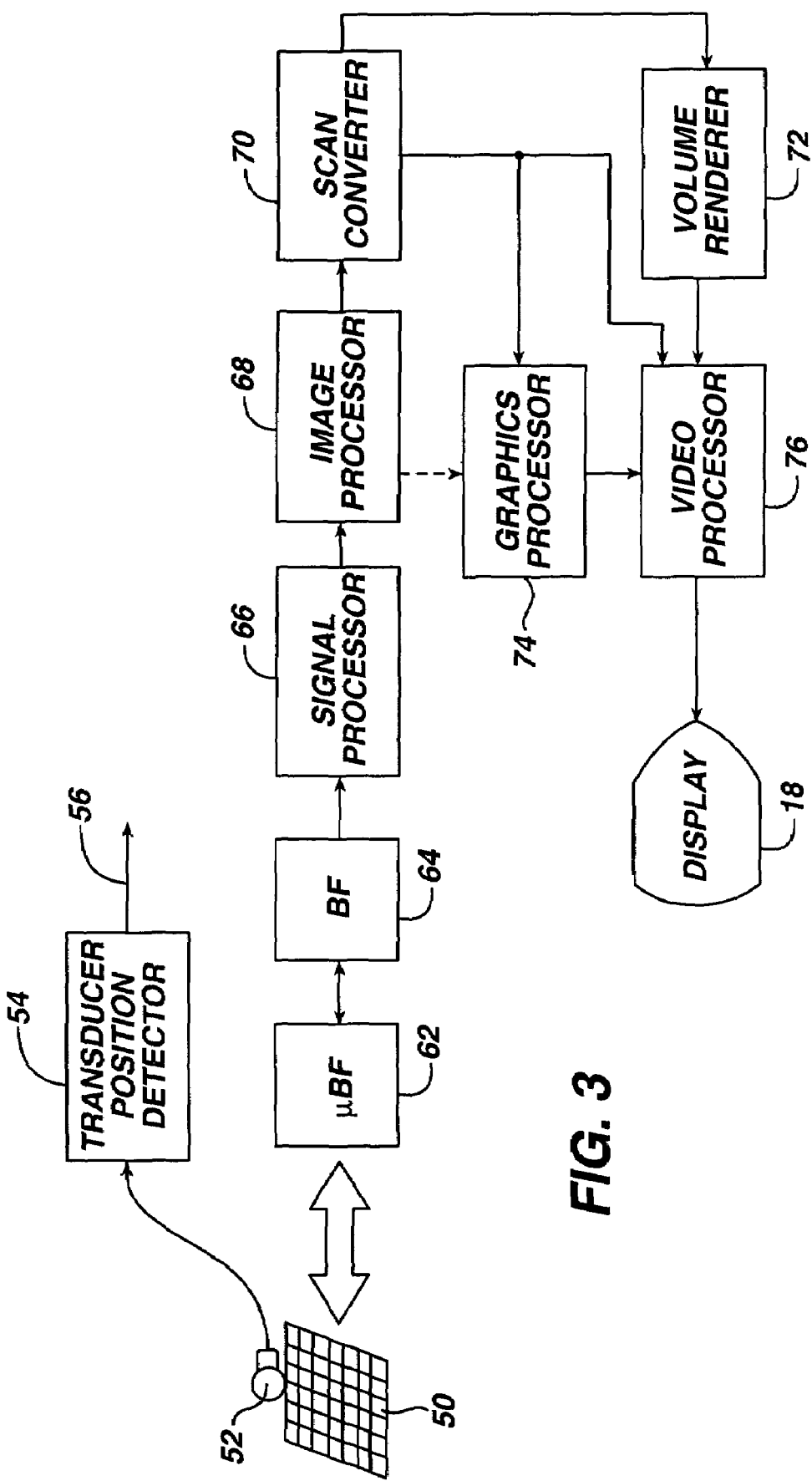
FIG. 3 illustrates in block diagram form the functional subsystems of a three dimensional ultrasonic imaging system suitable for use in an embodiment of the present invention.

FIG. 3 illustrates some of the components of the 3D ultrasound system of FIG. 1 in further detail. The elements of a two dimensional array transducer 50 are coupled to a plurality of microbeamformers 62. The microbeamformers control the transmission of ultrasound by the elements of the array transducer 50 and partially beamform echoes returned to groups of the elements. The microbeamformers 62 are preferably fabricated in integrated circuit form and located in the housing of the probe 10 near the array transducer. Microbeamformers, or subarray beamformers as they are often called, are more fully described in U.S. Pat. Nos. 6,375,617 and 5,997,479. The probe 10 may also include a position sensor 52 which provides signals indicative of the position of the probe 10 to a transducer position detector 54. The sensor 52 may be a magnetic, electromagnetic, radio frequency, infrared, or other type of sensor such as one which transmits a signal that is detected by a voltage impedance circuit. The transducer position signal 56 produced by the detector 54 may be used by the ultrasound system or coupled to the interventional device system when useful for the formation of spatially coordinated images containing information from both systems.

The partially beamformed signals produced by the microbeamformers 62 are coupled to a beamformer 64 where the beamformation process is completed. The resultant coherent echo signals along the beams are processed by filtering, amplitude detection, Doppler signal detection, and other processes by a signal processor 66. The echo signals are then processed into image signals in the coordinate system of the probe (r,θ,φ for example) by an image processor 68. The image signals are converted to a desired image format (x,y,z Cartesian coordinates, for example) by a scan converter 70. The three dimensional image data is coupled to a volume renderer 72 which renders a three dimensional view of the volumetric region 120 as seen from a selected look direction. Volume rendering is well known in the art and is described in U.S. Pat. No. 5,474,073. Volume rendering may also be performed on image data which has not been scan converted as described in U.S. [patent application Ser. No. 10/026,996, filed Dec. 19, 2001 by Alistair Dow and Paul Detmer.] During two dimensional imaging the image plane data bypasses the volume renderer and is coupled directly to a video processor 76 which produces video drive signals compatible with the requirements of the display 18. The volume rendered 3D images are also coupled to the video processor 76 for display. The system can display individual volume rendered images or a series of volume rendered images showing the dynamic flow and motion of the anatomy being imaged in real time. In addition, two volume renderings can be done of a volumetric data set from slightly offset look directions, and the two displayed simultaneously on a stereoscopic display as described in U.S. Pat. [application Ser. No. 60/43,096, filed Dec. 3, 2002 by Jonathan Ziel and entitled "Method and Apparatus to Display 3D Rendered Ultrasound Data on an Ultrasound Cart in Stereovision"]. A graphics processor 74 receives either scan converted image data from the scan converter 70 or unscan-converted image data from the image processor 68 for analysis and the generation of graphics, such as visual emphasis of the tip of an interventional device or the detection of the border of an organ within the image field. The visual emphasis may be provided by an enhanced or unique brightness, color, or volume rendering process for imaging the tip of the device, for example. The resultant graphics are coupled to the video processor where they are coordinated and overlaid with the image for display.

Figure 4:
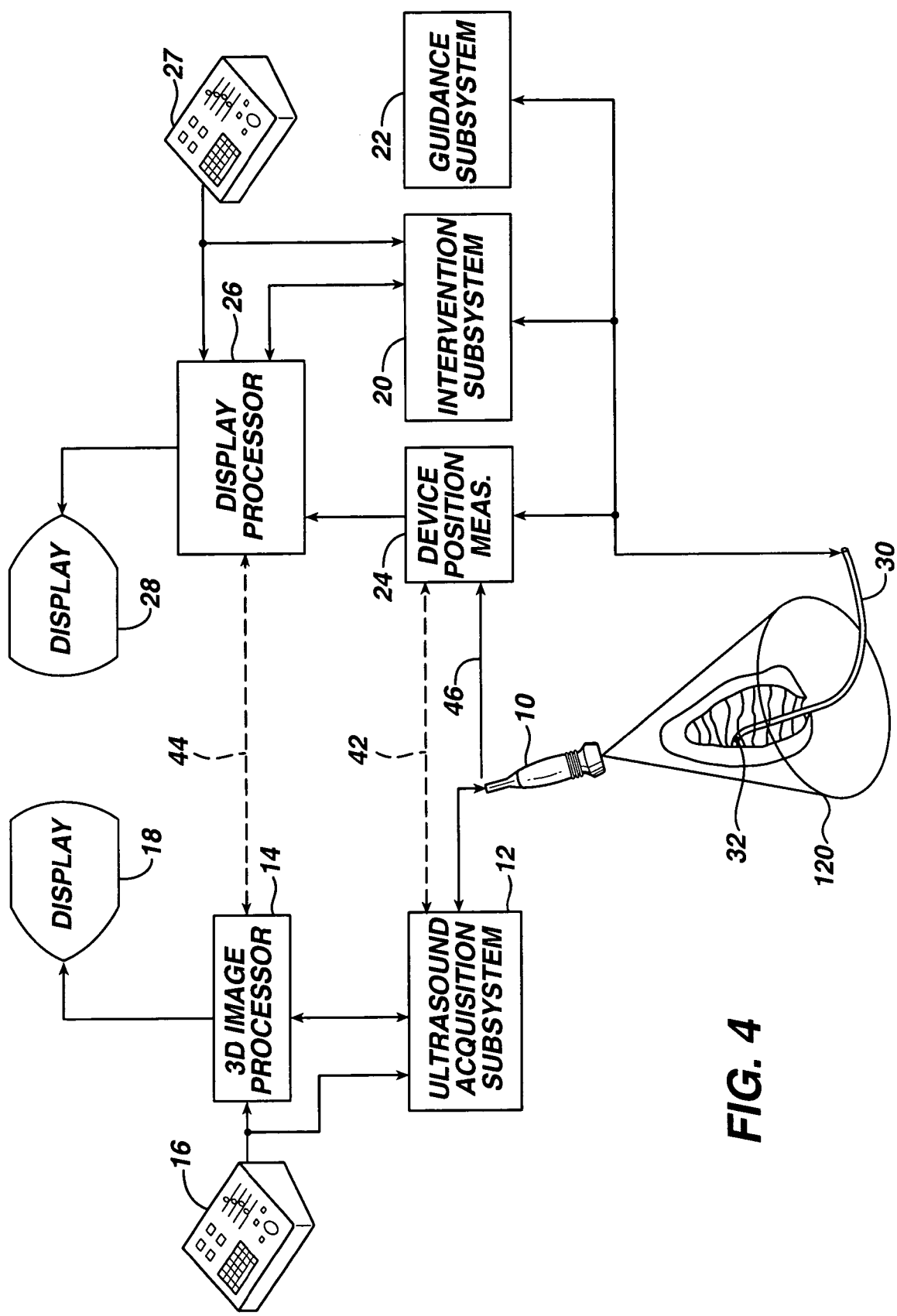
FIG. 4 illustrates in block diagram form another embodiment of the use of three dimensional ultrasonic imaging to guide or monitor an invasive instrument and procedure.

FIG. 4 illustrates another embodiment of the present invention. This embodiment differs from that of FIG. 1 in that there is a connection 46 from the probe 10 to the device position measurement subsystem 24 of the interventional device system. In this embodiment the probe 10 includes the position sensor 52. Rather than process the probe position signal by the transducer position detector 54 in the ultrasound system, the signal is processed by the same subsystem that processes the position signal from the interventional device 30. The two position signals allow a direct correlation of the positions of the interventional device and the probe to be performed by the interventional device system and used for coordinated imaging of the two systems.

Figure 5:
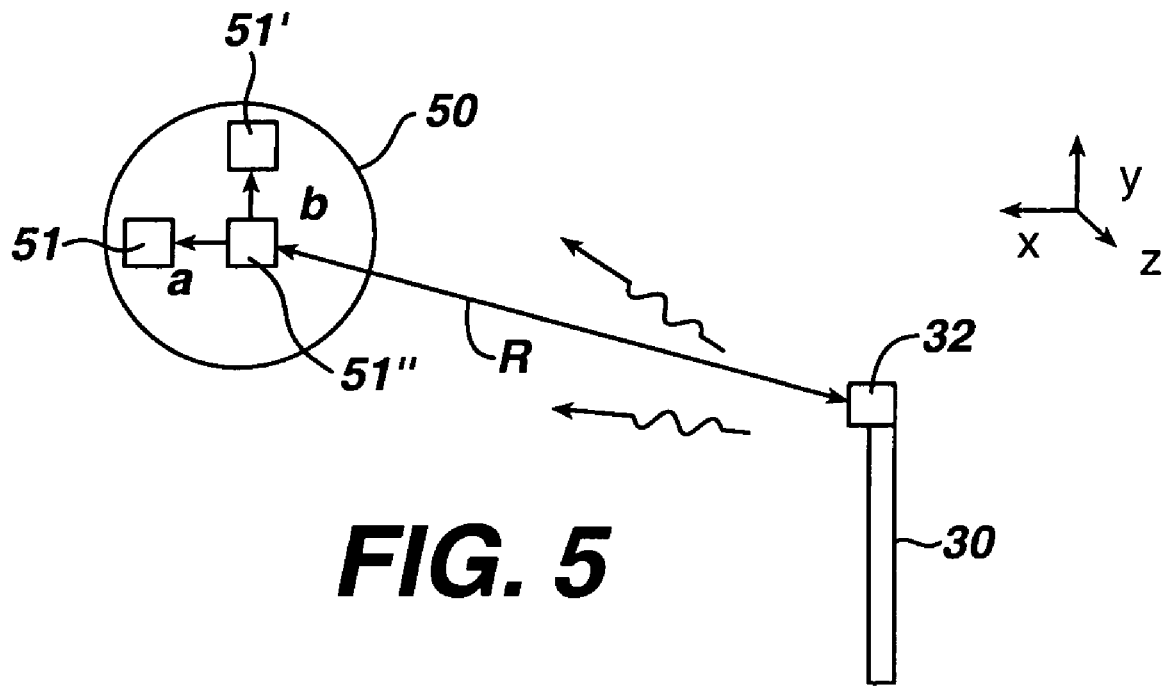
FIG. 5 illustrates a method for positionally locating an invasive medical device within the body by means of a two dimensional array transducer.

FIG. 5 illustrates one technique by which the position of the interventional device 30 is detected by the probe 10. In the drawing a transducer 32 located on the interventional device 30 transmits an acoustic pulse which is received by three elements 51, 51' and 51" of the transducer array 50. The elements 51 and 51' are spaced apart from element 51" by known distances a and b. By measuring the times of arrival of the pulse from the interventional device at the three elements the position of the transducer 32 with respect to the array transducer 50 can be calculated by triangulation. This can be performed by computing $$x\_position = (a^2 + v^2(t_0^2 - t_a^2))/2a$$

$$y\_position = (b^2 + v^2(t_0^2 - t_b^2))/2b$$

$$z\_position = \sqrt{v^2 t_0^2 - x\_position^2 - y\_position^2}$$

where $t_0$ is the time of flight of the pulse to element 51", $t_a$ is the time of flight to element 51 and $t_b$ is the time of flight to element 51' and v is the speed of sound (approximately 1550 m/sec) in the body.

Figure 6:
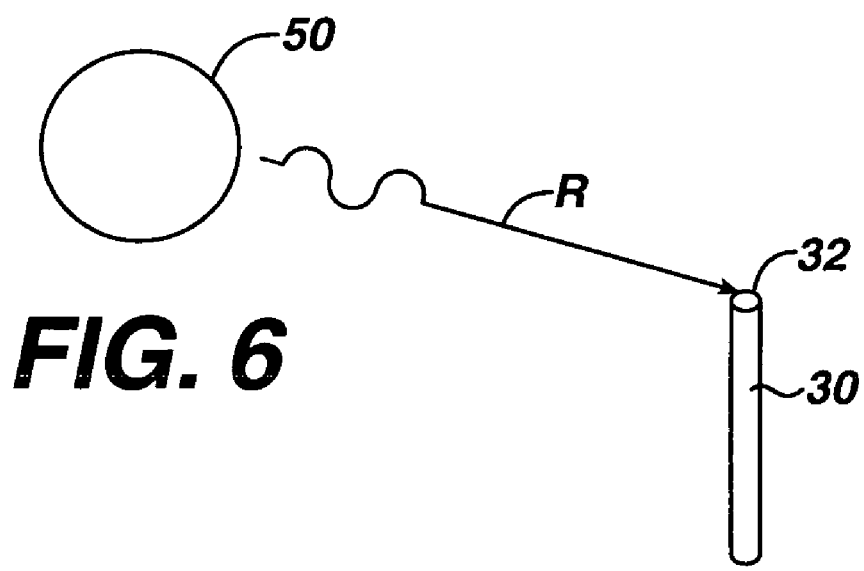
FIG. 6 illustrates a second method for positionally locating an invasive medical device within the body.

FIG. 6 illustrates a technique for locating the position of the interventional device in which ultrasound pulses from the imaging probe 10 are received by a transducer 32 on the interventional device 30. The transducer 32 listens for pulses from the probe 10. The transmit beam with the strongest signal or the shortest time of flight to the transducer 32 corresponds to the direction of the transducer 32 with respect to the transducer array 50. The distance R between the probe 10 and the transducer 32 is determined by the time of flight of the transmitted pulse. In this embodiment the connection 46 or the synchronizing line 42 would be used to exchange the times of transmission and/or reception information between the ultrasound system and the interventional device system.

An interventional device with its own ultrasonic transducer can be used to provide other locational information. For instance, if the interventional device has an ultrasonic transducer which is capable of transmitting and receiving from a distal end of the device, the transducer can be used for ranging, sending out pulses and receiving echoes from targeted tissues or tissue interfaces and thereby monitoring or measuring or displaying the distance between a distal part of the device and nearby anatomy from the time-of-flight of the transmit-receive interval. In one embodiment of such a device, the operator can visually observe the device approaching the tissue of interest in the three dimensional image, and can also observe a measure of the distance between the device and the tissue. The distance measure can for example be displayed numerically in centimeters, or in a quantified display such as an M-mode display, in which the progressive closure of the device with the tissue can be seen over an interval of time.

The location of the interventional device may also be detected if desired by signal and/or image processing techniques in the ultrasound system. For example, the use of a highly reflective element on the interventional device 30 such as a diffraction grating as shown in U.S. Pat. No. 4,401,124 may be used to produce a distinctly identifiable echo return from the interventional device. Alternatively if the interventional device has excessive specular reflective characteristics, it may be desirable to use a device which provides better scattering and/or absorption of ultrasound energy, such as one with a roughened or absorptive surface. This would allow the system gain to be increased for better definition of the tissue structure in the 3D image, while at the same time the interventional device does not overwhelm the image with bright, strongly reflected echoes. Another alternative is to identify the shape of the interventional device tip by image processing such as automated border detection of the tip in the images. Yet another approach is to cause the tip of the interventional device to be vibrated so that it produces a Doppler return as described in U.S. Pat. No. 5,095,910. Other embodiments using transducers on the interventional device may be found in U.S. Pat. Nos. 5,158,088 and 5,259,837. Other sensor types for invasive devices such as magnetic field coils may be employed as described in U.S. Pat. No. 6,332,089.

Figure 7:
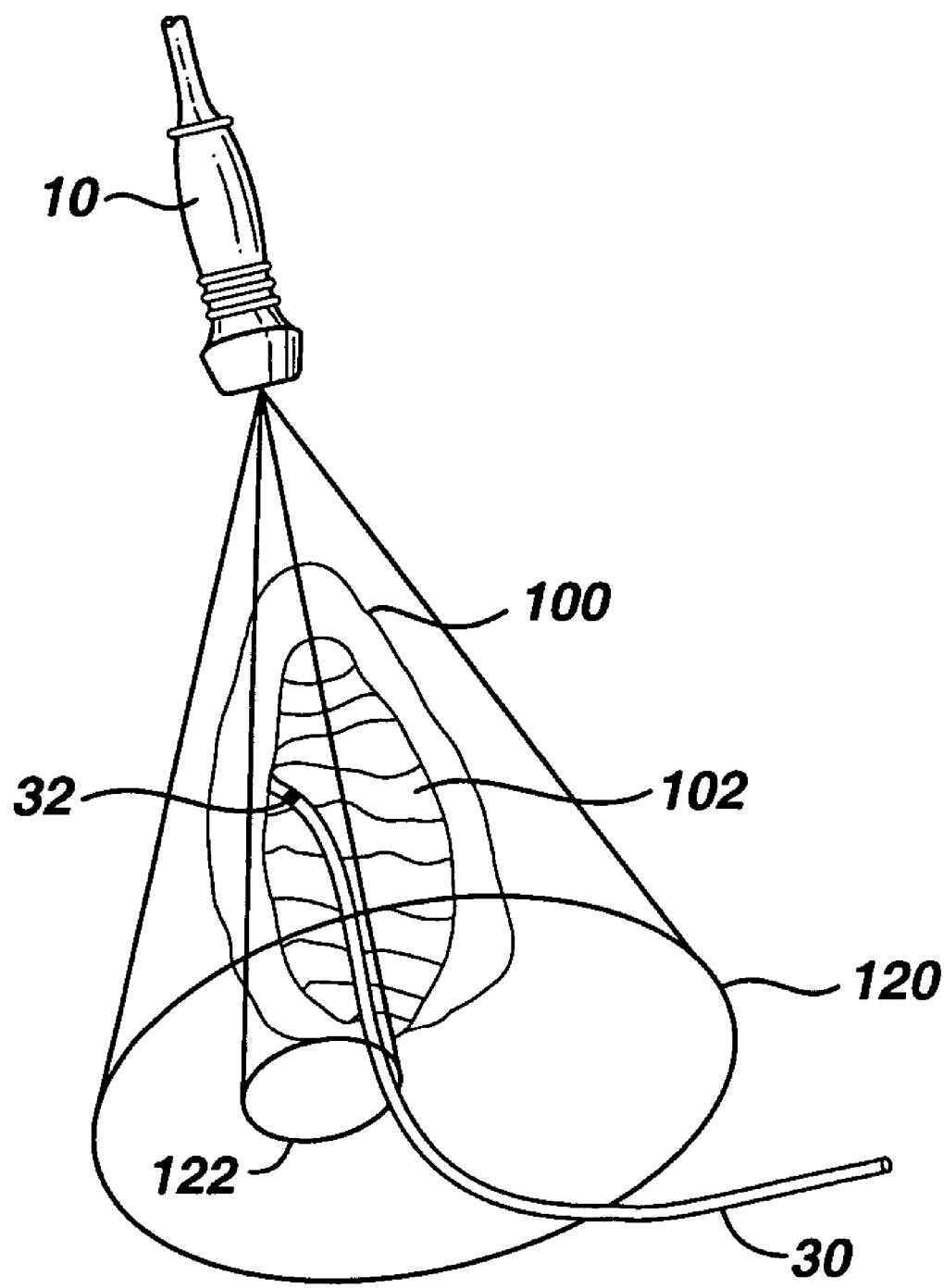
FIG. 7 illustrates the scanning of the volume around an invasive device with greater beam density than the surrounding image volume.

One of the difficulties when conducting 3D ultrasonic imaging of interventional devices is that a wide or deep volumetric field of view is usually required to adequately image the device in the environs of its path of travel and procedure. This means that a significant number of beams must be transmitted and received to adequately scan the volumetric field of view with the desired resolution and without spatial aliasing. Furthermore, the depth of the field of view requires significant times of travel of the transmitted pulses and received echoes. These characteristics cannot be avoided as they are mandated by the law of physics governing the speed of sound in the body. Accordingly a significant amount of time is needed to acquire a full three dimensional image, and the frame rate of display will often be lower than desired. FIG. 7 illustrates one solution to this dilemma, which is to use a different scanning methodology in the vicinity of the interventional device 30 than is employed in the outer reaches of the wide field of view. In the illustrated example, the location of the interventional device is determined by one of the techniques discussed above. This information is communicated to the ultrasound acquisition subsystem 12, when then transmits a greater beam density in the volumetric region 122 surrounding the interventional device 30. In the remainder of the volumetric field of view 120 more widely spaced transmit beams are employed. The space between the widely spaced transmit beams may be filled in by interpolating synthetic echo signals if desired. By this technique the volumetric region 122 surrounding the interventional probe will be shown with higher definition and resolution, enabling the physician to accurately guide and use the device at the site of the procedure. The remaining volumetric space will be shown with less definition but sufficient to orient the interventional device and procedure in the surrounding tissue. The beam density within the volumetric region of the interventional device can be uniformly high with the surrounding space scanned with uniformly lesser beam density. Alternatively, the highest beam density can be employed in the vicinity of the device sensor 32, with the beam density declining with greater distances from the intentional device. By continuously tracking the location of the interventional device 30 the volumetric region 122 is constantly redefined as needed to spatially correspond to the location of the interventional device 30.

Another variation in beam density which may be employed is to use different orders of received multilines in the proximity of the interventional device and in the surrounding volume. Variation in multiline order and transmit beam density can be used together or separately. For example the same spatial transmit beam density can be used throughout the scanned volume, but higher order multiline (a greater number of differently steered receive lines for each transmit beam) is used in the vicinity of the interventional device than in the surrounding volume to produce a more detailed image in the region of the interventional device. As a second example, a lesser spatial transmit beam density is used in the surrounding volume than is used in the vicinity of the interventional device. Higher order multiline is then used in the surrounding volume to fill in the spaces between transmit beam axes with a relatively large number of received multilines and a lower order of multiline reception is used in the vicinity of the interventional device to fill in the lesser spacing between transmit beam axes with a relatively fewer number of received multilines for each transmit beam. This latter approach will reduce the multiline artifact of echo intensity variation as a function of the distance of each received multiline from the transmit beam axis in the vicinity of the interventional device where a more detailed view is desired.

Figure 8:
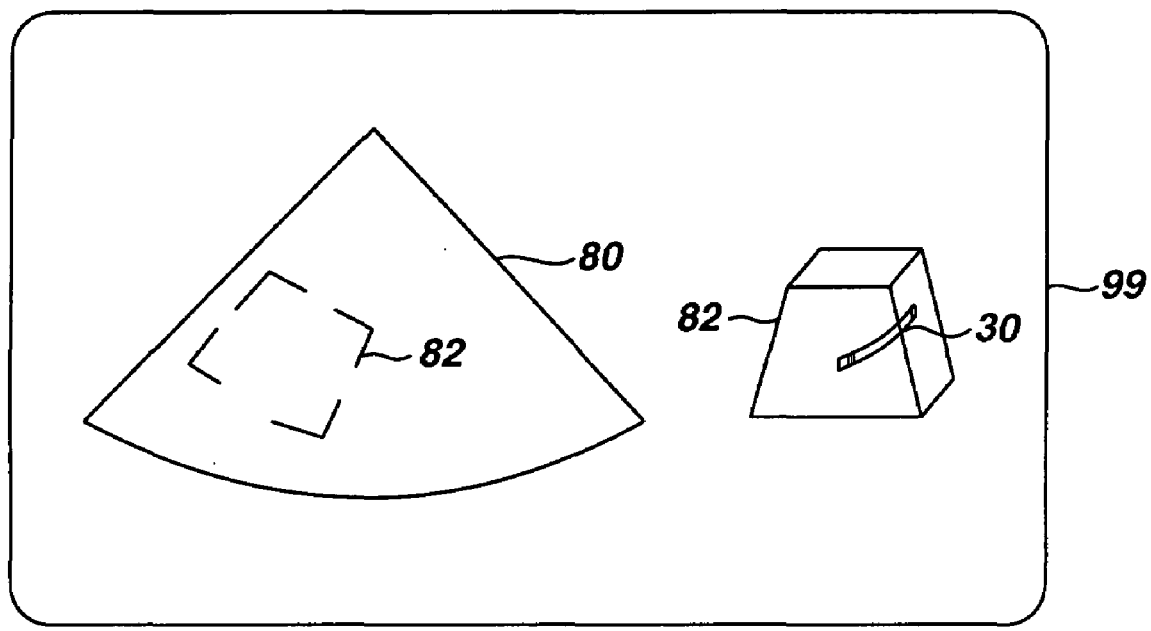
FIGS. 8-11 illustrate ultrasound displays of a volume of interest together with a greater volumetric field of view containing the volume of interest.
Figure 9:
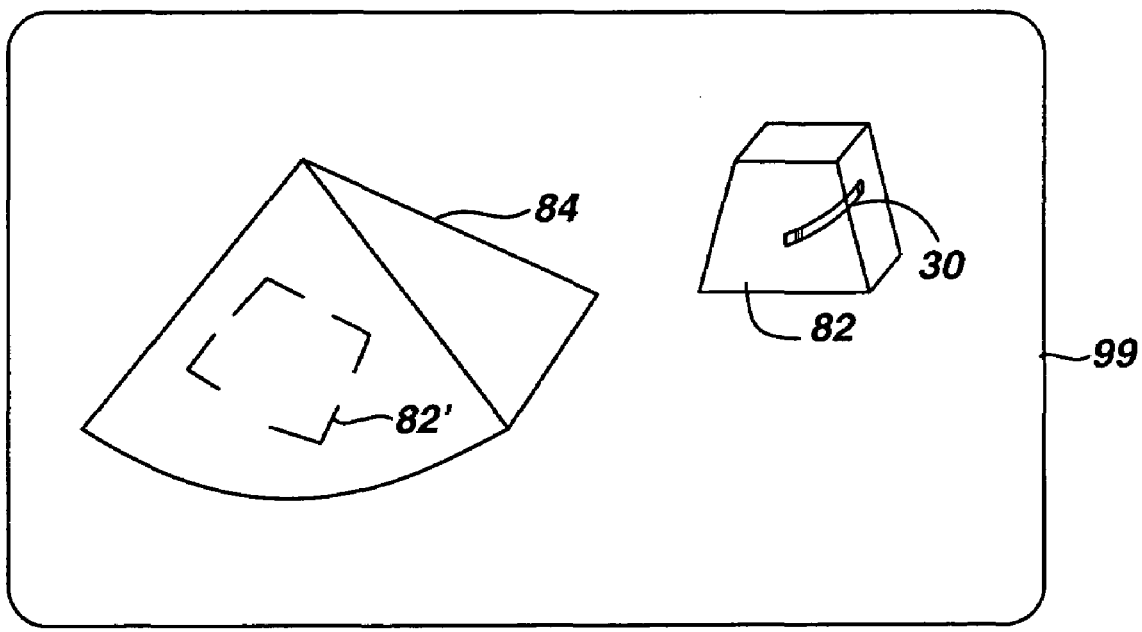
Figure 10:
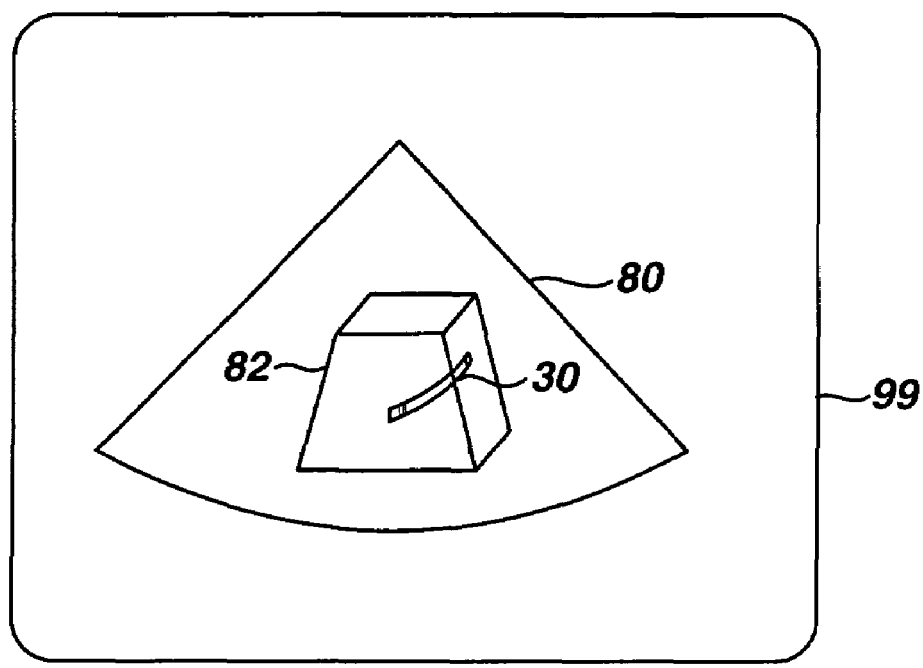
Figure 11:
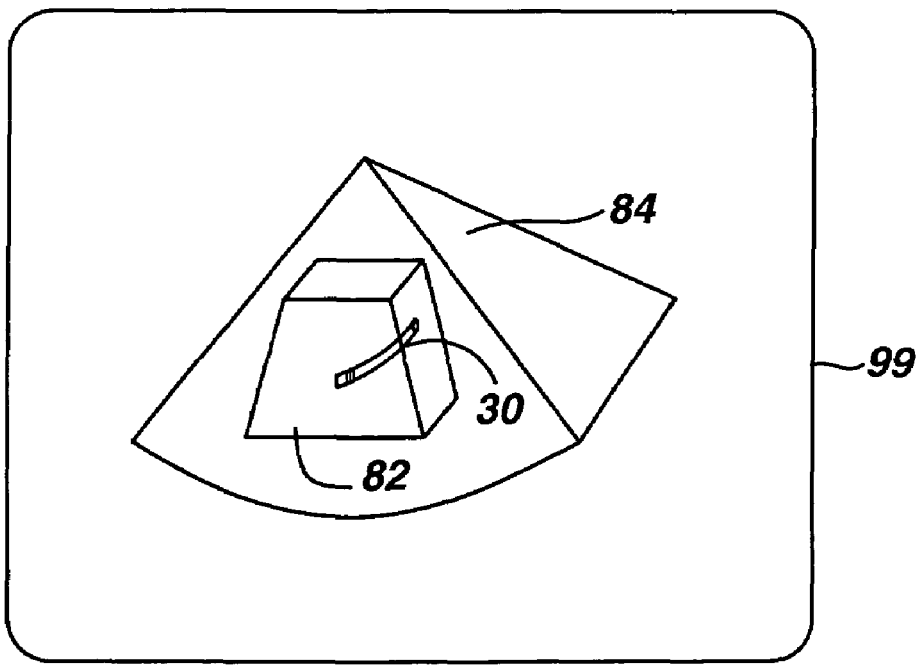

FIGS. 8-13 illustrate displays 99 of other techniques for dealing with this problem of 3D frame rate decline. In FIG. 8 the 3D locus 82 of the interventional device 30 is scanned with a high beam density and/or frame rate. The volumetric region 82 is shown in the same display 99 with a wider planar field of view 80. The plane 80 may be scanned less frequently or with a lesser beam density than that of the volumetric region 82 of the device 30. Different orders of multiline reception may also be employed. Scanning the area 80 with a lesser beam density means that a greater volume or area can be scanned with the same number of transmit-receive cycles as were needed to scan the higher beam density volume 82. Thus a wider field of view can be scanned with lesser beam density and the frame rate of the full image shown in FIG. 8 is increased. An outline 82' depicts the location of the interventional device volume 82 in relation to the image plane 80. In FIG. 9 the wider field of view is provided by a 3D image 84 with a lesser beam density and/or frame rate than that of the separate interventional device volume 82. The location of the interventional device volume 82 in relation to the greater volume image 84 is indicated by the outline 82'. In FIG. 10 the interventional device volume 82 is shown in its correct spatial location in relation to the image plane 80. In FIG. 11 the interventional device volume 82 is shown in its true spatial position in the more lightly sampled volume 84, the approach depicted in FIG. 7.

Figure 12:
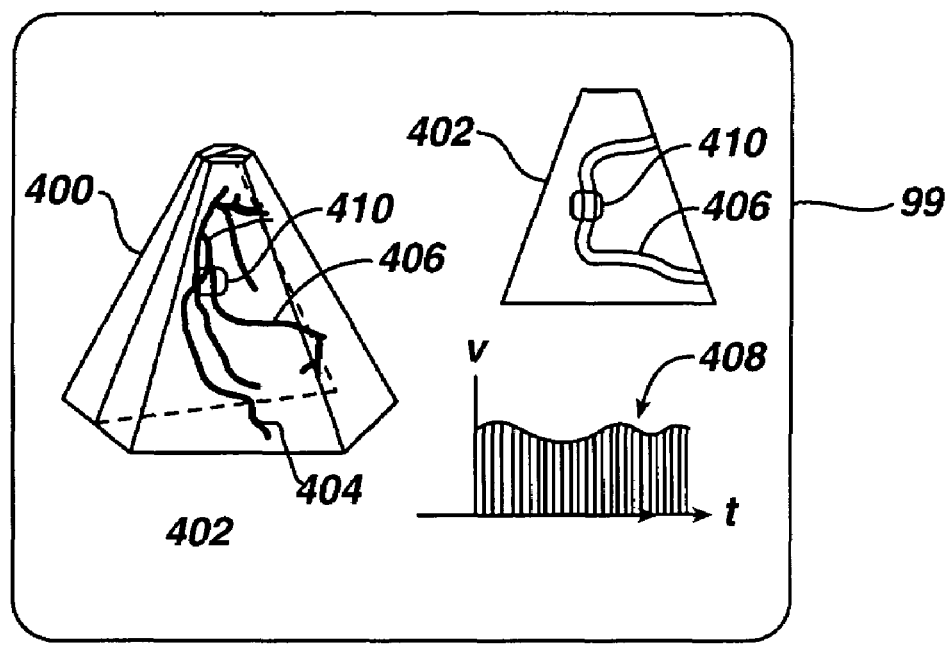
FIG. 12 illustrates the display of three dimensional, two dimensional, and quantified ultrasonic measures of an interventional site.

FIG. 12 illustrates a display 99 of a three dimensional ultrasonic image 400 of a system of vasculature 404,406. An interventional procedure such as the placement of a stent has been performed at a location 410 that is recorded in the image. The location 410 was marked by detecting the location of the interventional device at the time of the setting of the stent and is thereafter continuously shown in its recorded spatial location in the body. The three dimensional image 400 provides a comprehensive view of the locus of the stent, and is produced with a lower beam density and/or frame rate than that of a plane 402 of the volumetric region 400. The image of the plane 402 is shown adjacent to the volumetric field of view and contains the locational marker 410. By scanning this image plane 402 with a greater beam density and/or a higher frame rate the physician is better able to observe the result of the interventional procedure. In addition, an image 408 particular to the procedural site location 410 is shown in the display. This will typically be a time-based display such as an EKG trace, a spectral Doppler display, an M-mode display, or a color M-mode display, all of which provide physiological information as a function of time.

Figure 13:
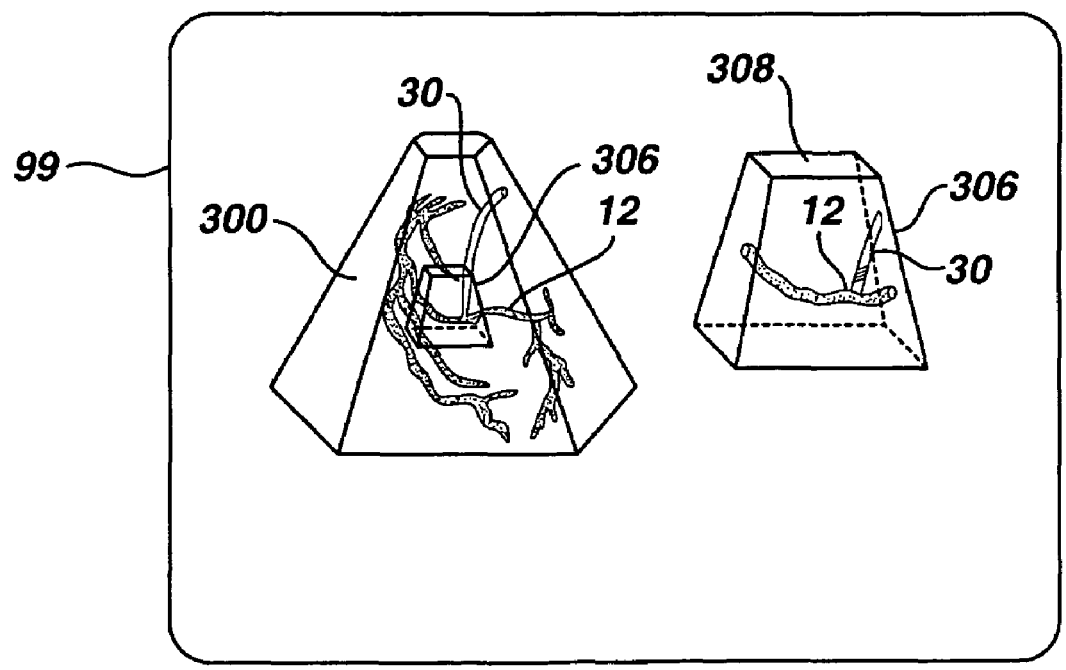
FIG. 13 illustrates the display of a detailed three dimensional ultrasonic image of an interventional device along with a greater volumetric view of the location of the interventional device.

FIG. 13 illustrates a display 99 employing the techniques shown in FIGS. 9 and 11. In this display a wide field of view three dimensional hexagonal image 300 which is scanned at a lesser beam density and/or frame rate reveals the expanse of a vasculature system 12. An interventional device 12 performing a procedure at a point in the vasculature is shown in a more highly resolved volumetric region 306. The interventional device volume 306 is also shown separately in the same display in a zoomed view 308 in which the point of the procedure is shown in greater detail. This embodiment combines several of the features of the earlier embodiments. Other variations will readily occur to those skilled in the art.

Figure 14:
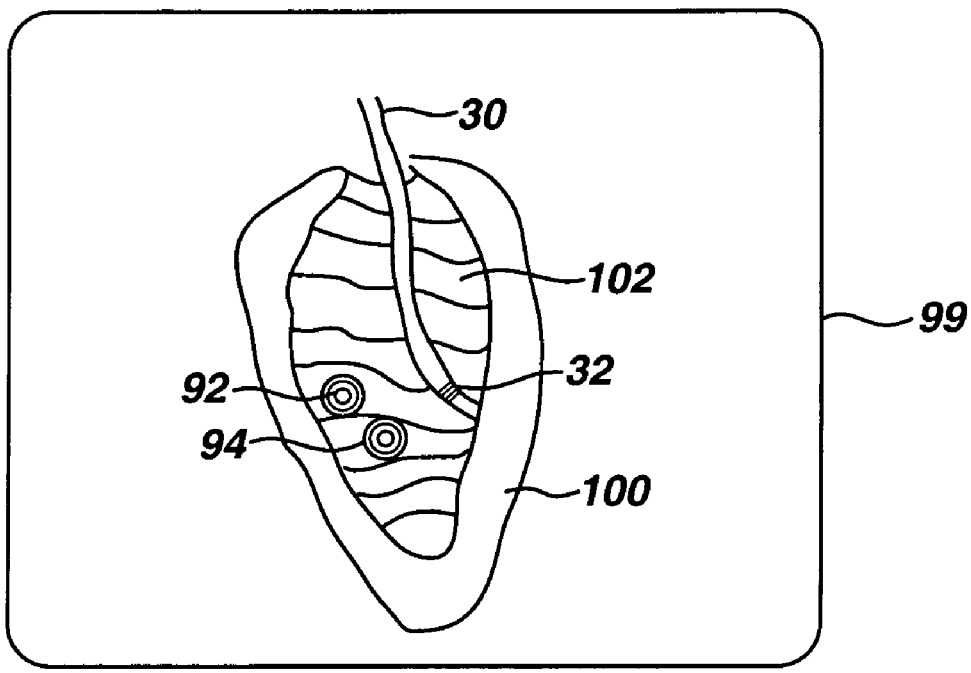
FIG. 14 illustrates the recording of the locus of interventional procedures in a three dimensional ultrasonic image.

FIG. 14 illustrates an embodiment of the present invention in which the results of an invasive treatment regime are recorded in a three dimensional ultrasonic image. This drawing illustrates a catheter 30 with a working tip which ablates lesions on the heart wall. As each lesion is treated the location of the treatment is marked by use of the position sensor 32 or one of the interventional device detection techniques discussed above. Another technique for detecting the position of the catheter is to apply electrodes of different voltages to opposite sides of the body to create a spatial voltage gradient across the body. The sensor 32 detects the impedance at its location in the gradient field, which corresponds to the spatial location of the catheter working tip. By using multiple electrodes at different times and places on the body, the location of the working tip can be sensed in three dimensions. These treatment locations are stored in memory and can be used to map the general region where the treatment occurred, such as the heart wall. In accordance with a further aspect of the present invention, the treatment location information is merged with the three dimensional ultrasonic image data to visually mark the treatment locations on the endocardial wall as shown by the circular markers 92,94 in FIG. 14. Recording the sequence of live three dimensional ultrasound images not only records the activity of the interventional device but also the progress and history of the treatment procedure.

Figure 15:
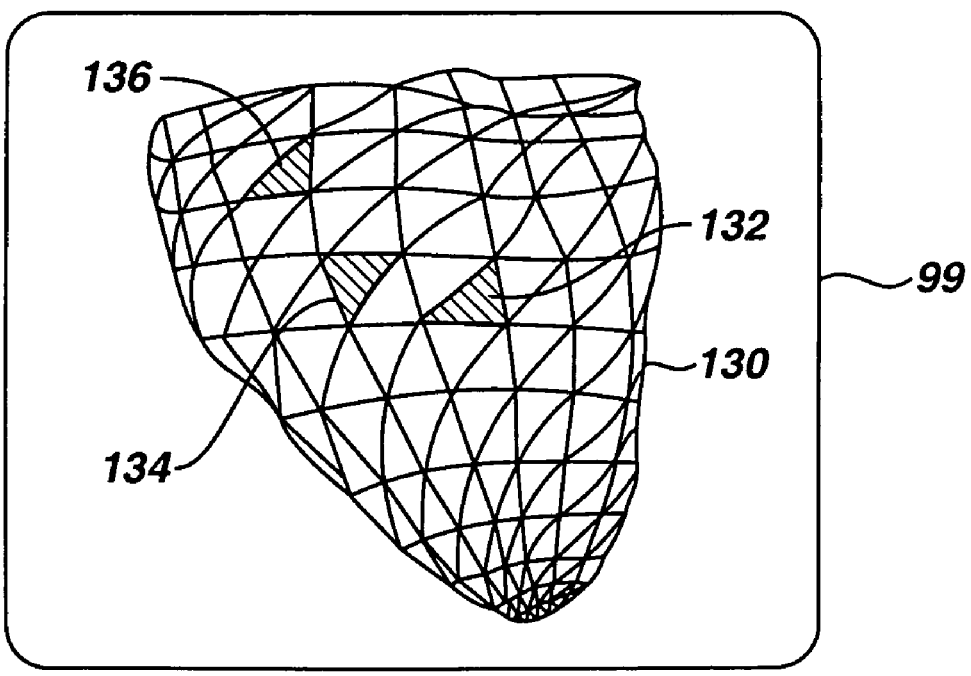
FIG. 15 illustrates the recording of the loci of interventional procedures in a wire frame model derived from three dimensional ultrasonic image data.

FIG. 15 illustrates an embodiment in which the progress and history of the treatment procedure is recorded on a model of the anatomy being treated, in this case a wire frame model 130. This wire frame model 130 is of the heart wall of the left ventricle, and may be formed by border detection of the three dimensional data set as described in U.S. Pat. No. 6,491,636 (Chenal et al.) or in U.S. Pat. No. 5,601,084 (Sheehan et al.) or published European patent specification EP 0 961 135 B1 (Mumm et al). As treatment procedures are performed at specific points on the heart wall, those locations are detected by use of the sensor 32 or one of the interventional device detection techniques discussed above. Those locations 132, 134,136 are then recorded in the proper spatial locations on the 3D wire frame model 130, where they may appear as unique colors or intensities. The wire frame model may be a live, real time model which moves in correspondence with the moving heart, or it may be a representation of the heart intermediate the heart's shape and size at end systole and end diastole, or it may be a wire frame model of the heart at its moment of greatest expansion at end diastole.

Figure 16:
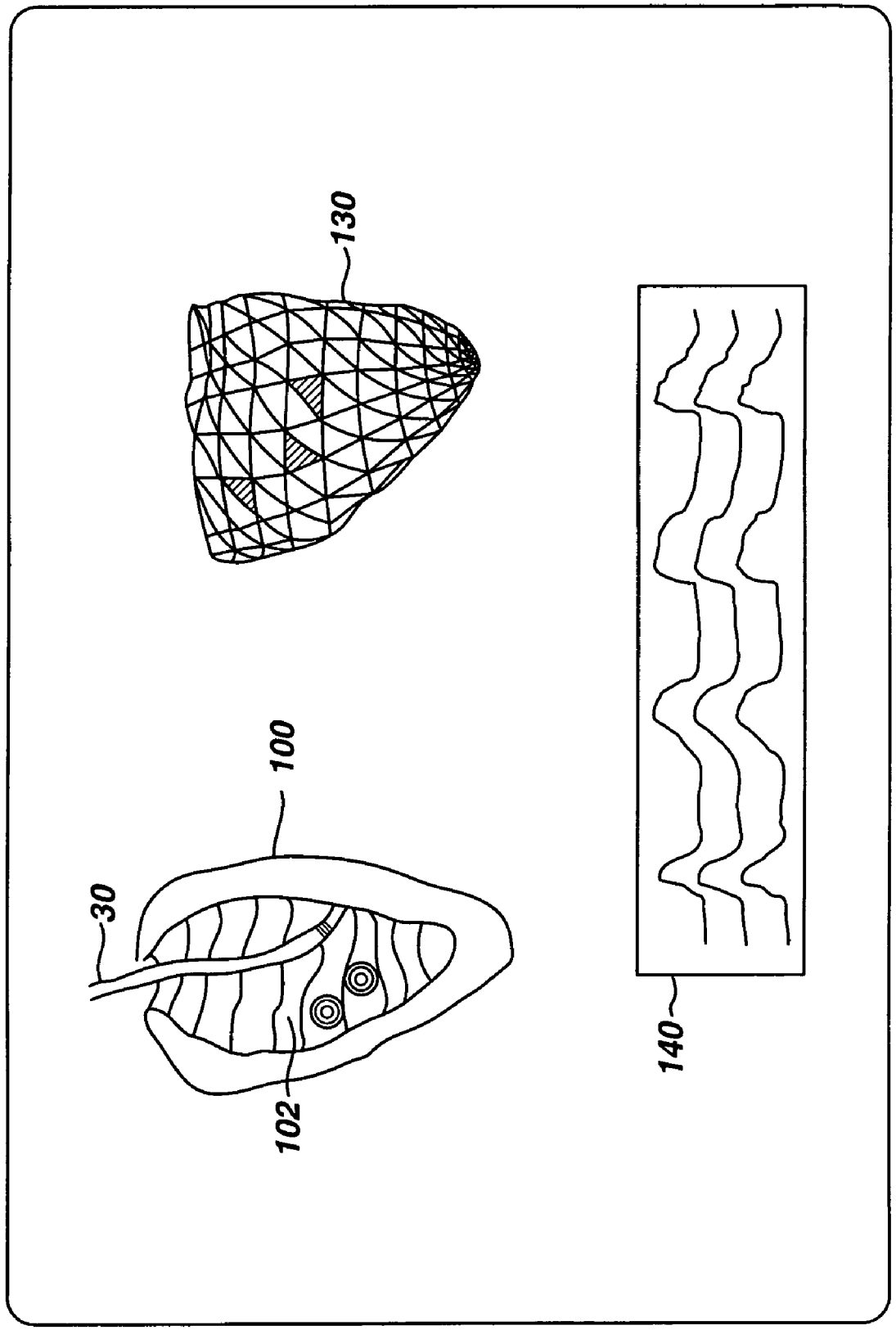
FIG. 16 illustrates a simultaneous view of a live three dimensional image of an interventional device, a wire frame model recording the loci of interventional procedures, and ECG waveforms relating to the loci.

FIG. 16 illustrates a display screen 99 which shows cardiac information in three ways: a live three dimensional image 100 of the heart and an interventional device 30, a wire frame model 130 of the chamber of the heart undergoing treatment, and multiple ECG traces 140 taken at points of the heart designated by the interventional device 30. The separate ECG traces may be labeled, colored, or visually designated in some other way to show correspondence with the locations at which they were acquired, which locations may also be shown by markers on the three dimensional ultrasonic image 100, the wire frame model 130, or both. Such a display enables visual monitoring of the live procedure, a visual record of the procedures performed, and measurement data acquired at the sites of the procedures.

Figure 17:
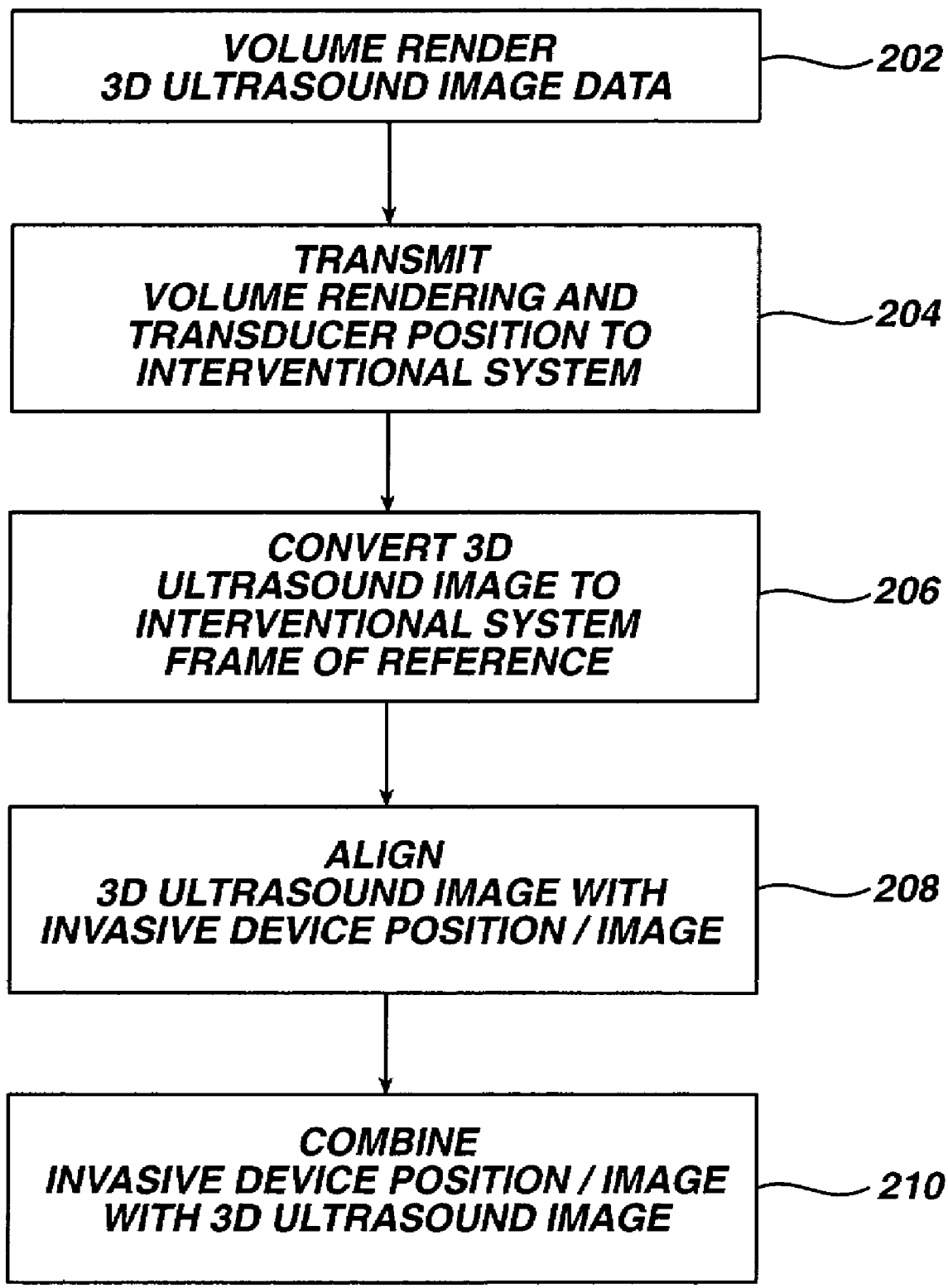
FIGS. 17-21 are flowcharts illustrating methods for combining image and/or locational data from a three dimensional ultrasonic imaging system and an interventional system.

FIGS. 17-21 are flowcharts which illustrate several ways in which the three dimensional ultrasonic image data acquired by the ultrasound system can be merged with spatially based data of the interventional device such as location or image data. In the process of FIG. 17 acquired 3D ultrasound data is volume rendered by the ultrasound system to form a 3D ultrasound image in step 202. In step 204 the volume rendered ultrasound image and data identifying the position of the array transducer 50 or probe 10 is transmitted to the interventional system. In step 206 the 3D ultrasound image is converted to the frame of reference of the data of the interventional system. This may involve rescaling the coordinate data of the 3D ultrasound image to match the coordinate scaling of the interventional system data. Once the ultrasound Image data has been converted, the ultrasound image and the interventional device data are aligned (step 208) through the use of the probe and interventional device coordinate information and combined (step 210) to form a consolidated three dimensional image for display 28 containing spatially accurate information about the interventional device and/or its procedure.

Figure 18:
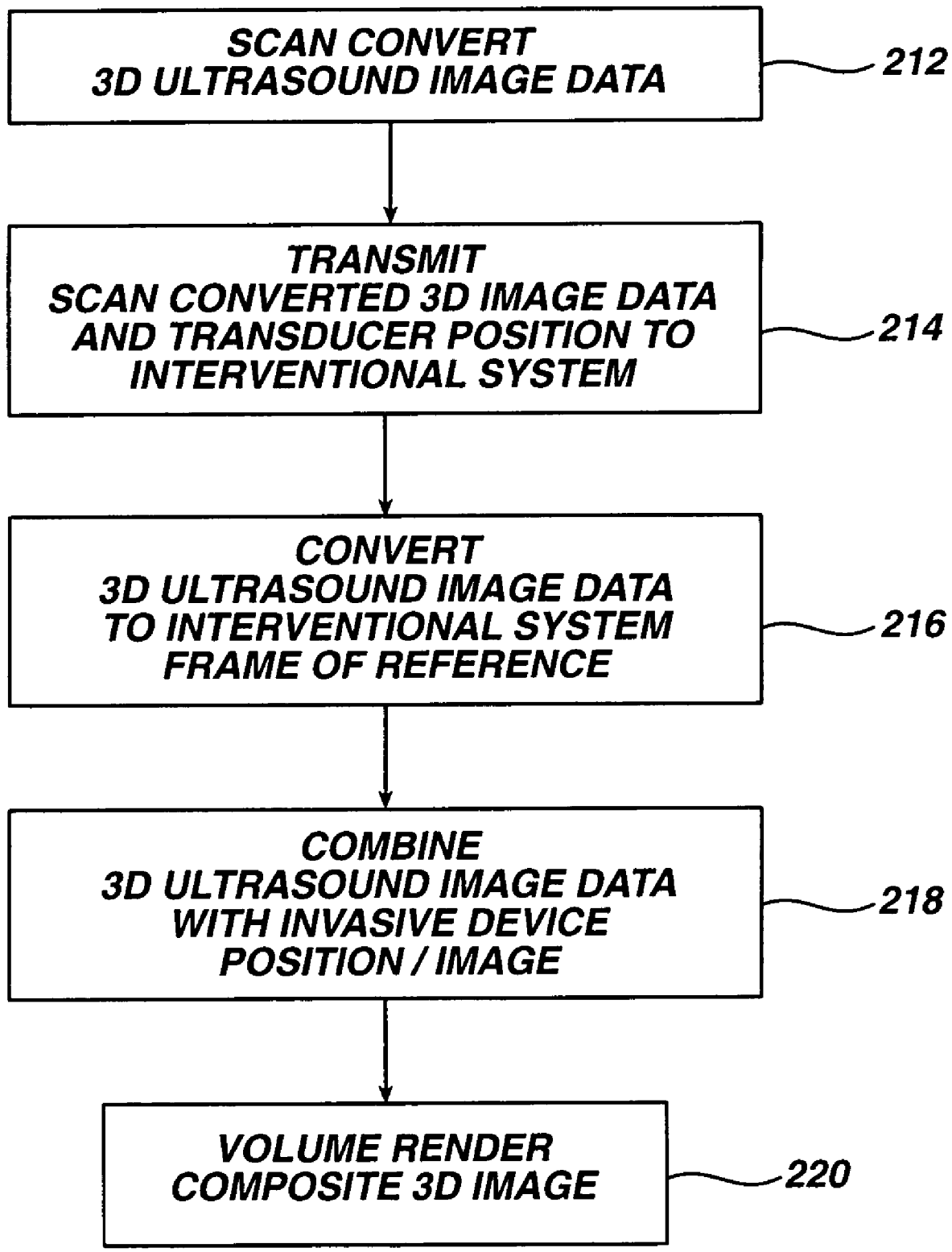

In the process of FIG. 18 there is no initial volume rendering of the 3D ultrasound image data. Instead, the process begins in step 212 with the scan conversion of the 3D ultrasound image data to form a Cartesian referenced 3D data set. In step 214 the scan converted 3D data set and the probe or array transducer position information is transmitted to the interventional system. In step 216 the 3D ultrasound image data is converted to the frame of reference of the data of the interventional system. Again, this may be done by rescaling the coordinate data of the 3D ultrasound image to match the coordinate scaling of the interventional system data. In step 218 the 3D image data set and the interventional device data are combined on the basis of their common reference frame. The merged data sets are then volume rendered by the interventional system in step 220 to produce a composite three dimensional ultrasonic image containing spatially accurate information about the interventional device and/or its procedure.

Figure 19:
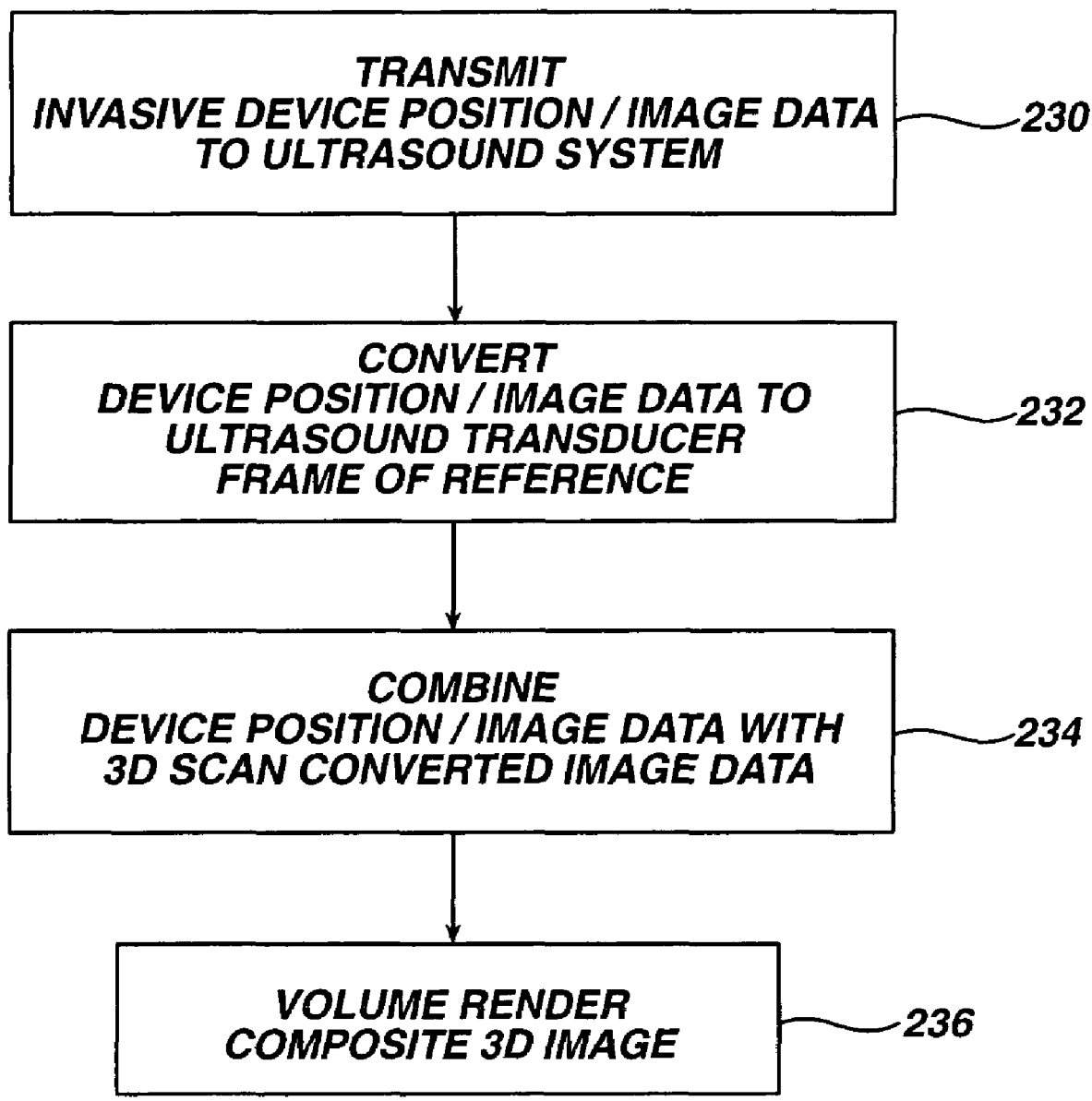

In the process of FIG. 19 the data acquired by the interventional device, such as position or image data, is transmitted to the ultrasound system in step 230. In step 232 the interventional device data is converted to the frame of reference of the ultrasound probe or transducer as by rescaling the data. In step 234 the interventional device data is combined with 3D scan converted ultrasonic image data. In step 236 the combined data is volume rendered to form a three dimensional ultrasonic image containing spatially relevant information from the interventional system. The images thus produced are displayed on the ultrasound system display 18.

Figure 20:
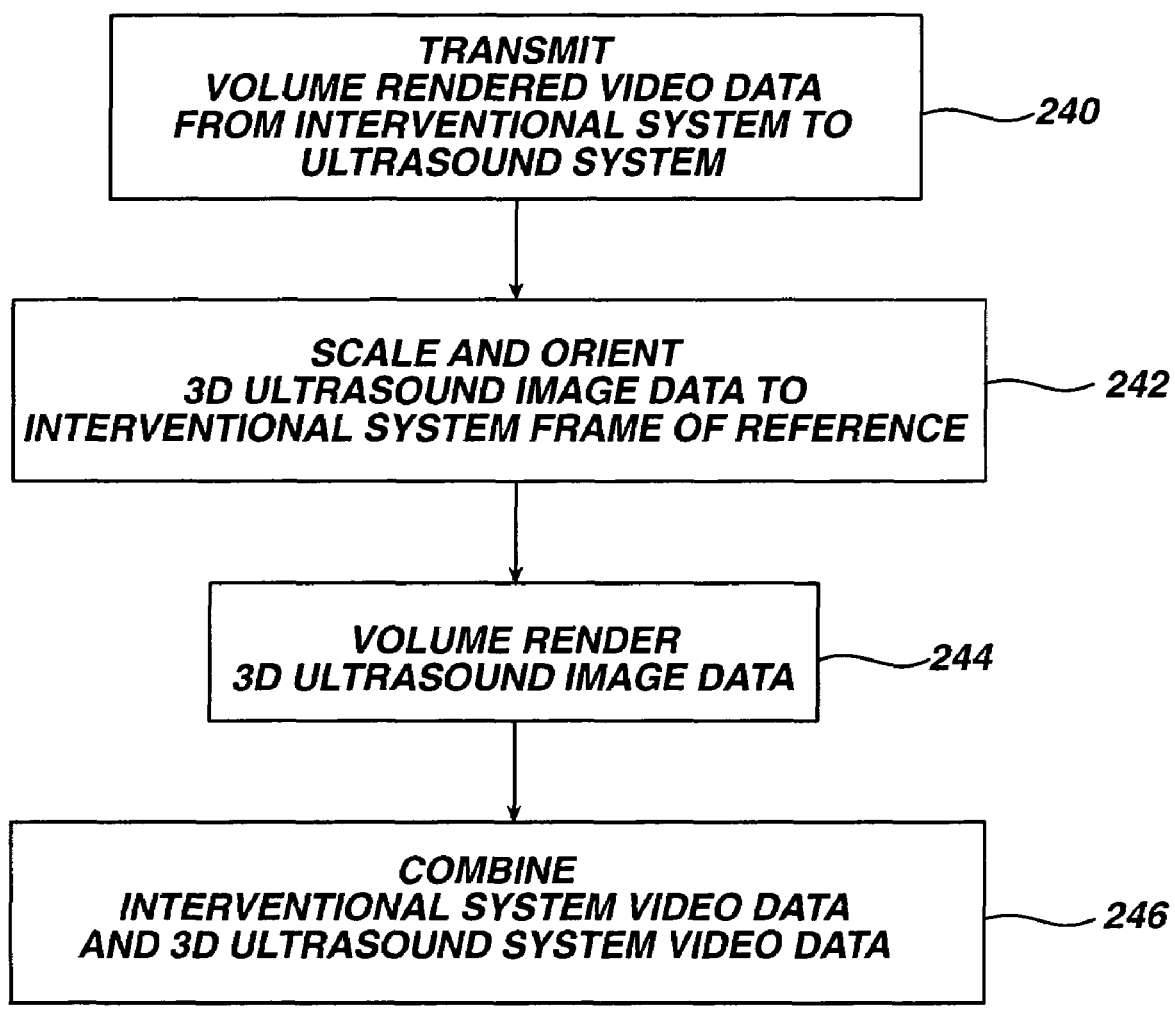

In the process of FIG. 20 volume rendered video data produced by the interventional system is transmitted to the ultrasound system in step 240. In step 242, three dimensional ultrasound image data is rescaled and oriented to match the frame of reference of the interventional system data. The three dimensional ultrasound image data is then rendered in step 244 from the frame of reference or perspective that was used in the rendering of the interventional system data. The interventional system video data and the 3D ultrasound image data, now rendered to the same frame of reference, may now be combined to form a consolidated three dimensional image in step 246.

Figure 21:
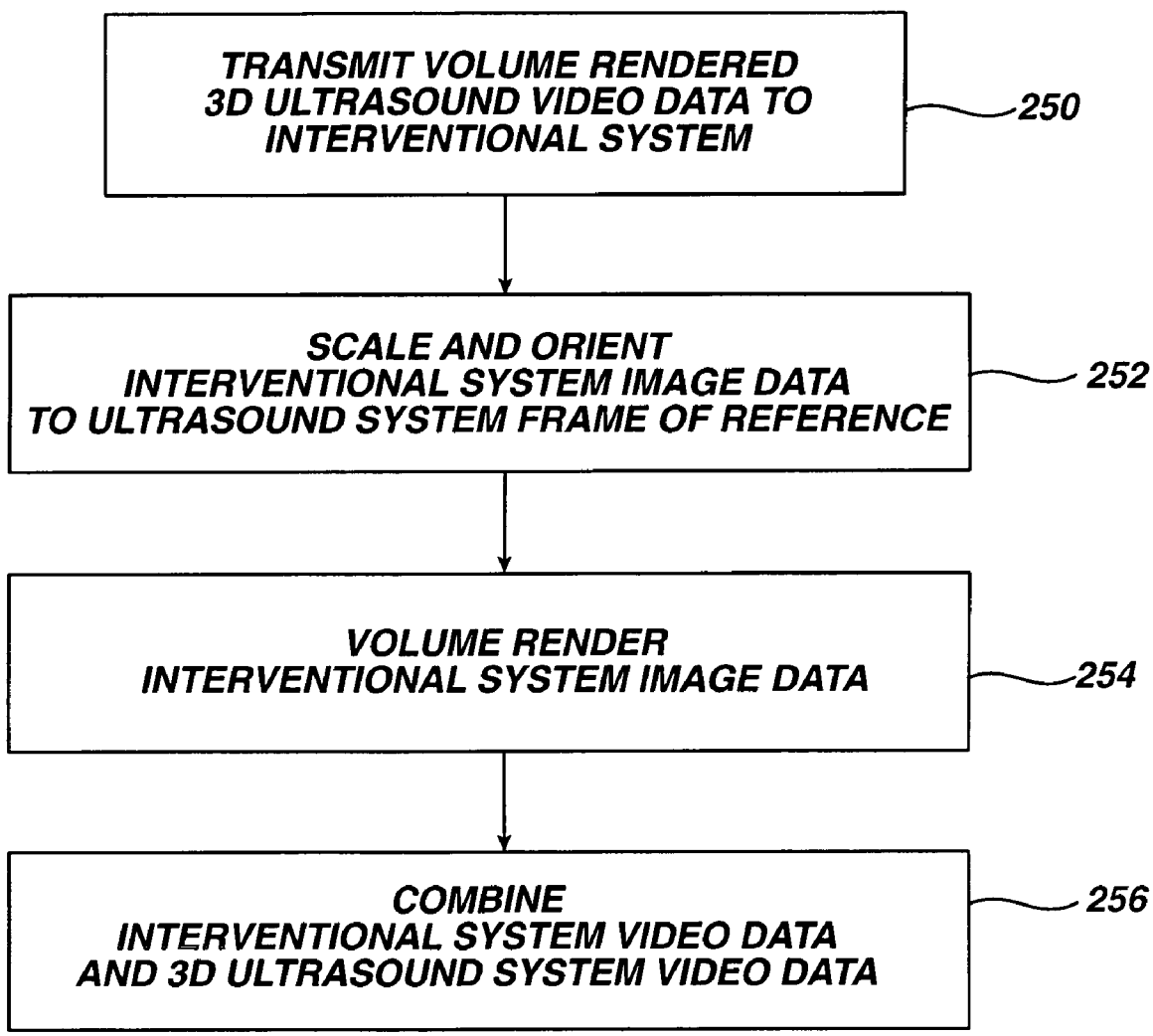

In the process of FIG. 21 volume rendered 3D ultrasound video data is transmitted to the interventional system in step 250. In step 252 interventional system image data is rescaled and oriented to the frame of reference of the 3D ultrasound rendering. In step 254 the interventional system image data is rendered to the same frame of reference as that of the 3D ultrasound image. In step 256 the commonly referenced interventional system video data and the 3D ultrasound video data are combined into a consolidated image.

It will be apparent to those skilled in the art that three types of coordinate transformations between the three dimensional ultrasound data and the interventional device location data are possible. The interventional device data can be transformed to the coordinate system of the 3D ultrasound image, or the 3D ultrasound image data can be transformed to the coordinate system of the interventional device data, or both sets of data can be translated to a user-chosen scale or frame of reference.

Figure 22:
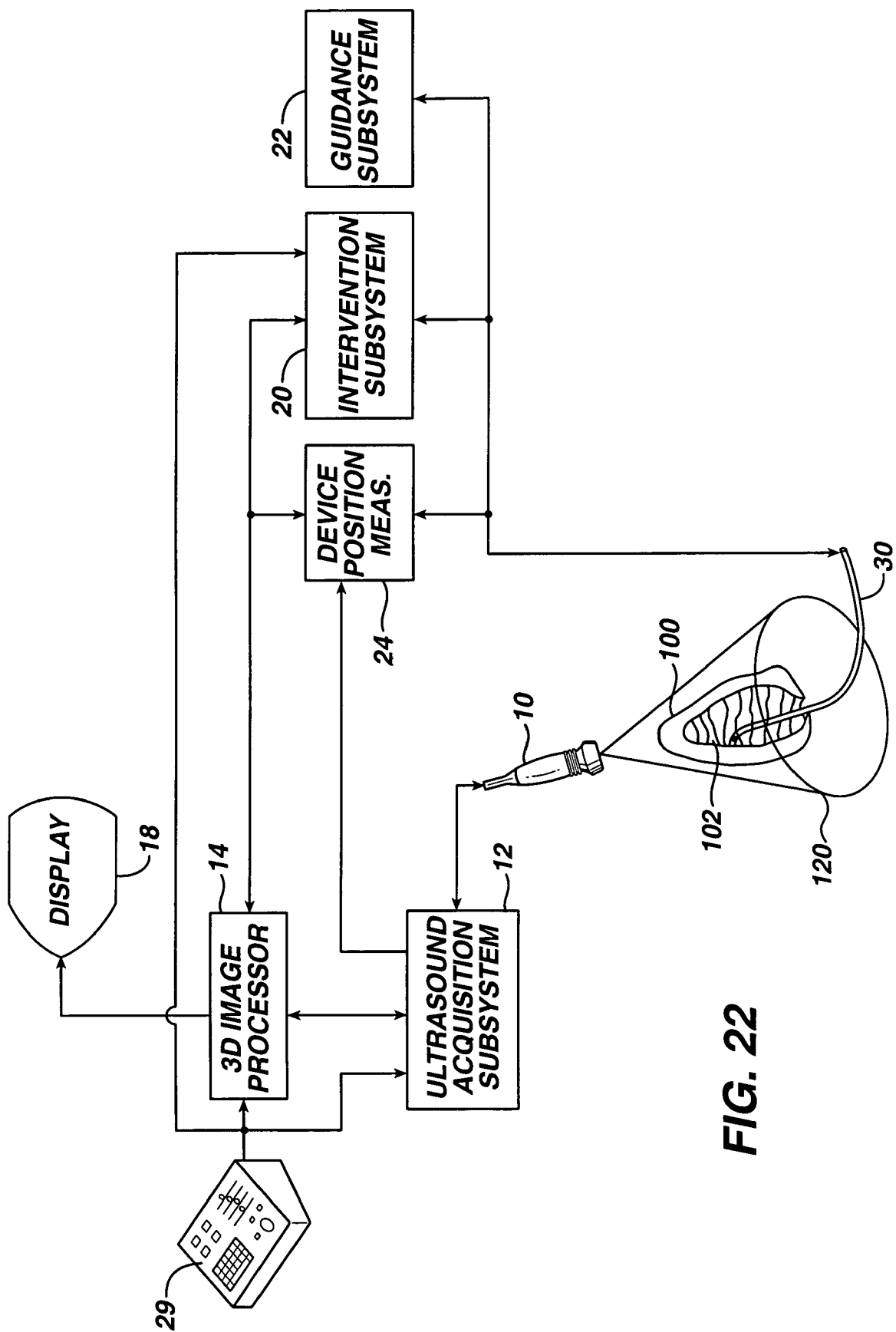
FIG. 22 illustrates in block diagram form a consolidated system for the conduct of an invasive procedure assisted by three dimensional ultrasonic imaging.

The principles of the foregoing data combining processes may be applied in the embodiment of FIG. 22 which is a combined 3D ultrasonic imaging and interventional device system. In this embodiment the interventional device 30 is manipulated by the guidance system 22 and operated to perform its procedure under control of the intervention subsystem 20. At times signaled by the intervention subsystem or the ultrasound acquisition subsystem the device position measurement subsystem 24 acquires locational information of the imaging probe 10, the interventional device 30, or both. The 3D ultrasonic image data acquired by the probe 10 and the ultrasound acquisition subsystem 12, and the interventional data acquired by the intervention subsystem, and the location data of the probe 10, the interventional device 30, or both, are then processed to form a consolidated 3D ultrasound image by the 3D image processor 14. The 3D image containing interventional device and/or procedure information is then displayed on the display 18. The entire imaging and interventional system is controlled by a user control panel 29.

As used herein the terms "surgical region", "surgical guidance", and "surgery" encompass any medical procedure in which a medical instrument or device is introduced into the body for a medical purpose.

What is claimed is:

1. A method of ultrasonically displaying an invasive medical device and the volumetric region of a body in which it is located comprising:
   scanning the volumetric region with beams transmitted by an ultrasonic array transducer;
   receiving echo signals from the volumetric region and from an invasive medical device located in the region;
   processing echo signals to produce a wide field of view of the volumetric region;
   processing echo signals to produce a detailed view of the portion of the volumetric region in which the invasive medical device is located; and
   displaying both the wide field of view of the volumetric region and the detailed view of the portion of the volumetric region in which the invasive medical device is located in spatial alignment in a common image on an image display.

2. The method of claim 1, wherein processing the echo signals to produce a wide field of view comprises processing the echo signals to produce a wide field of view two dimensional image; and
   wherein processing the echo signals to produce a detailed view comprises producing a volume rendering of a portion of the volumetric region.

3. The method of claim 2, further comprising designating the spatial location of the volume rendering in the two dimensional image.

4. The method of claim 2, wherein displaying further comprises displaying the wide field of view two dimensional image with the volume rendering in spatial alignment with and contained within the vide field of view image.

5. The method of claim 1, wherein processing the echo signals to produce a wide field of view comprises volume rendering the echo signals to produce a wide field of view three dimensional image; and
   wherein processing the echo signals to produce a detailed view comprises producing a volume rendering of a portion of the volumetric region.

6. The method of claim 5, further comprising designating the spatial location of the volume rendering of the portion of the volumetric region in the wide field of view three dimensional image.

7. The method of claim 5, wherein displaying further comprises displaying the wide field of view three dimensional image with the volume rendering of the portion of the volumetric region in spatial alignment with and contained within the wide field of view image.

8. The method of claim 7, wherein displaying further comprises displaying the volume rendering of the portion of the volumetric region in a separate enlarged or zoomed view.

9. The method of claim 1, wherein displaying further comprises displaying the detailed view of the portion of the volumetric region in a separate enlarged or zoomed view.

10. The method of claim 1, further comprising processing echo signals to produce a time-based display; and
    wherein displaying further comprises displaying the time-based display on an image display.

11. The method of claim 10, wherein processing echo signals to produce a time-based display further comprises processing echo signals to produce a spectral Doppler display, an M-mode display, or a color M-mode display.

12. The method of claim 1, wherein scanning further comprises transmitting a relatively low beam density over a volumetric region, with a relatively high beam density being transmitted in a portion of the volumetric region in which an invasive medical device is located.

13. The method of claim 12, wherein processing echo signals to produce a wide field of view further comprises processing echo signals received from a low beam density region of the volumetric region; and wherein processing echo signals to produce a detailed view further comprises processing echo signals received from a high beam density region of the volumetric region.

14. An ultrasonic surgical guidance imaging system which acts to guide the placement or observe the operation of an invasive medical device comprising:

an ultrasonic probe including an array transducer which steers ultrasonic beams over a volumetric surgical region which includes an invasive medical device;

a transmit beamformer coupled to the array transducer which acts to control the spatial beam density of the beams transmitted by the array transducer in the volumetric region;

a receive beamformer coupled to the array transducer and responsive to echo signals from array elements for the production of received scanlines in the vicinity of the invasive medical device and in the volumetric region at locations removed from the invasive medical device location;

an image processor responsive to the received scanlines for producing a wide field of view image of the volumetric surgical region and a detailed three dimensional view of the invasive medical device in a sub-region of the surgical region; and a display coupled to the image processor which displays the wide field of view image of the volumetric surgical region with the detailed three dimensional view of the sub-region of the invasive medical device in spatial registration with and contained within the wide field of view image.

15. The ultrasonic surgical guidance imaging system of claim 14, wherein the transmit beamformer acts to control the spatial beam density of the beams transmitted by the array transducer to be different in the vicinity of the invasive medical device than in the volumetric region at locations removed from the invasive medical device location.

16. The ultrasonic surgical guidance imaging system of claim 14, wherein the receive beamformer comprises a multiline receive beamformer.

17. The ultrasonic surgical guidance imaging system of claim 16, wherein the multiline receive beamformer is operated for the production of a different number of received multilines for each transmit beam in the vicinity of the invasive medical device than that produced in the volumetric region at locations removed from the invasive medical device location.

18. The method of claim 1, wherein displaying further comprises displaying the wide field of view of the volumetric region and the detailed view of the portion of the volumetric region at different frame rates of display.

19. The ultrasonic surgical guidance imaging system of claim 14, wherein the image processor is further operable to produce the wide field of view image and the detailed view at different frame rates of display.

* * * * *